United States Patent [19]

Cooney

[11] Patent Number: 4,795,457

[45] Date of Patent: Jan. 3, 1989

[54] VENOUS RESERVOIR

[75] Inventor: Catherine M. Cooney, Woburn, Mass.

[73] Assignee: C. R. Bard, Inc., Murray Hill, N.J.

[21] Appl. No.: 47,137

[22] Filed: May 8, 1987

[51] Int. Cl.$^4$ ............................................. A61B 19/00
[52] U.S. Cl. ......................................... 604/408; 604/7
[58] Field of Search ............... 604/317, 408, 410, 4–6; 128/762, 767, DIG. 3, DIG. 24; 383/107, 108

[56] References Cited

U.S. PATENT DOCUMENTS

| | | | |
|---|---|---|---|
| 3,985,135 | 10/1976 | Carpenter | 604/410 |
| 4,507,123 | 3/1985 | Yoshida | 604/408 |
| 4,622,032 | 11/1986 | Katsura | 604/4 |

OTHER PUBLICATIONS

"Fillet", American Heritage Dictionary, Houghton Mifflin, Boston, Mass., Second College Edition, p. 503, 1982.

"Extracorporeal Circulation in Open Cardiac Surgery", Travenol Laboratories, Morton Grove, Ill. (Pratt).

Primary Examiner—C. Fred Rosenbaum
Assistant Examiner—J. L. Kruter
Attorney, Agent, or Firm—Dennison, Meserole, Pollack & Scheiner

[57] ABSTRACT

A venous reservoir including a blood collecting chamber with heat seamed peripheral edges incorporating fillet-defining beads for enhanced blood flow and debubbling. Flow diverters are provided vertically between lower inlet tubes and upper air vents, and laterally between the inlet tubes and an outlet tube. The diverters are vertically spaced and upwardly inclined toward the vent within the flow path of the blood between the inlet and outlet tubes for an enhanced upward directing of entrapped air toward the vents and groove extensions thereof within the chamber.

26 Claims, 1 Drawing Sheet

VENOUS RESERVOIR

BACKGROUND OF THE INVENTION

The invention relates to venous reservoirs used in closed circuits for the temporary storage of blood, and is particularly concerned with a soft shell reservoir basically formed by a pair of overlapping thermoplastic or heat weldable resinous sheets joined along weld lines to define both a blood storage chamber and ancillary support structure. A reservoir of this general type, and the environment of the invention, will be noted in U.S. Pat. No. 4,622,032, Katsura et al, issued Nov. 11, 1986.

As blood enters such reservoirs, air is often entrained therein. Thus, it is essential that provision be made to effectively remove such air or air bubbles before the blood is returned to the patient. To this end, the reservoirs incorporate air vents, normally in the nature of tubes sealed to the reservoir and communicating with a high point of the collection chamber. However, in soft shell reservoirs in particular, problems arise in effecting a complete debubbling or air removal. Such problems can result from various factors including an inadequate flow pattern for the blood within the storage chamber, or the particular construction of the reservoir and chamber itself. In this latter case, a significant problem with regard to soft shell reservoirs is the tendency for air bubbles to collect along the heat sealed seams and the inability to adequately move these air bubbles to the air vent or vents for discharge. Typical examples of high-frequency welds in soft shell bags will be noted in U.S. Pat. No. 4,507,123, Yoshida, Mar. 26, 1985; and U.S. Pat. No. 4,548,023, Danby et al, Oct. 22, 1985.

SUMMARY OF THE INVENTION

It is the primary purpose of the present invention to provide a soft shell venous reservoir with an enhanced ability to debubble or remove air from the blood. In support of this goal, the collection space or chamber is specifically constructed to avoid potential air-trapping areas which are inherently defined along the seams of conventionally formed reservoir chambers. In doing so, the reservoir of the invention specifically eliminates the conventional restrictive edge passages or channels which both inhibit the smooth flow of blood and trap air, creating air pockets which tend to resist even specific efforts directed toward dislodging the air bubbles.

Basically, the invention proposes formation of the welded edge seams with a bead of a size to completely bridge the formed inwardly directed angle in the manner of a fillet whereby flow restricting constructions between the panels at the joinder are eliminated. This in turn enhances the smooth flow of blood along the edges of the chamber and substantially reduces any tendency for the trapping of air bubbles therealong.

The effective debubbling of the blood is further encouraged by the incorporation of means within the chamber which, through a selective change in the flow pattern, helps ease any air which might have been introduced through the patient lines to the top of the chamber for removal through the air vents. The vented removal of the air from the top of the chamber is essential in preventing exiting of the air through the blood outlet and possibly making its way to the patient.

The overall shape of the reservoir chamber is such as to provide the best flow pattern with low venous resistance at the desired volume capacity. Basically, the cardiotomy inlet and the blood inlet communicate with the bottom of the chamber within an upwardly directed well. The air vents communicate with the upper end of the chamber in general vertical alignment over the inlets with at least one vent at the high point of the chamber. The blood outlet tube also communicates with the bottom of the chamber laterally of the inlets and, similarly, within a well-like depression. The inlet and outlet tubes are separated by an intermediate ridge precluding direct flow therebetween. The flow controlling means for enhancing the upward movement of air bubbles comprises three vertically spaced diverters in the nature of oblong buttons defined by a welding of the reservoir panels to each other. These diverters are in a vertical line laterally offset from the general linear alignment of the inlet tubes and the vents, and positioned so as to disrupt the normal flow of blood between the inlets and outlet. Each diverter is upwardly inclined toward the vents, thereby tending to upwardly direct any air contained within the blood flow as the flow is momentarily disrupted as it moves to the outlet tube.

The interior of the chamber will incorporate a pair of vertically elongate flat channels aligned with the vents to assist in movement of the air to the vents while preventing any tendency for the bag panels to close on themselves and create air pockets. In view of the flexible nature of the soft shell reservoir, it is also considered desirable to provide a pair of stiffeners in the form of rigid PVC tubes slidably received within a pair of full height sleeves formed along the opposed vertical edges of the reservoir laterally outward of the blood chamber.

Other objects and advantages of the invention will be appreciated from the details of construction and manner of use of the reservoir as more fully hereinafter described and claimed.

DESCRIPTION OF PREFERRED EMBODIMENT

Referring now more specifically to the drawings, the venous reservoir 10 is a soft shell reservoir of rectangular configuration formed of two thin transparent sheets of an appropriate thermoplastic material such as polyvinyl chloride (PVC) having a preferred thickness of 0.017" each. The sheets are sealed to each other at selected locations by radio frequency (RF) welding to basically define a central blood collecting space or chamber 12 and two vertical edge sleeves 14 in lateral outwardly spaced relation to the chamber 12.

Figure 1:
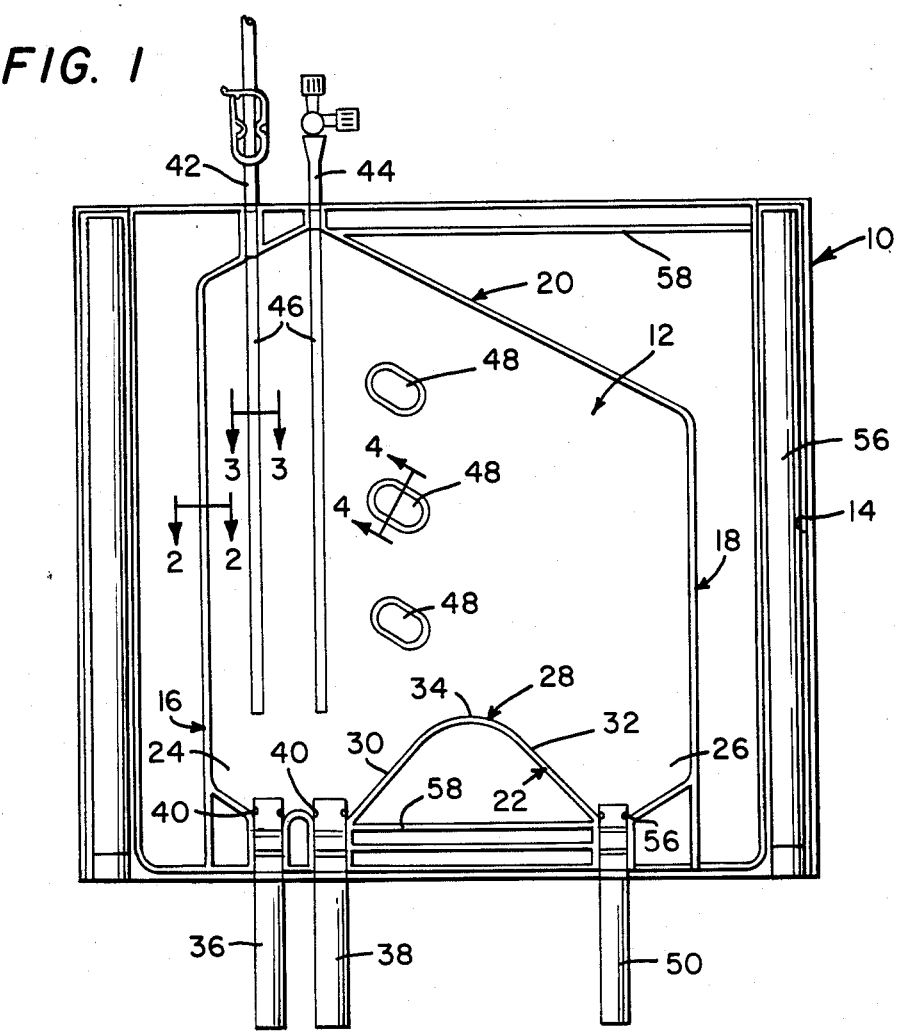
FIG. 1 is an elevational view of the venous reservoir of the invention.

The collecting chamber 12, assuming vertical orientation of the reservoir 10 as illustrated in FIG. 1, includes opposed vertical side seams 16 and 18 and a top seam 20 peaking at a point laterally closer to the side seam 16 than the side seam 18.

The bottom of the chamber 12 is formed by a bottom seam 22 configured to define a pair of laterally spaced upwardly opening inlet and outlet wells 24 and 26 with a central ridge 28 therebetween. The ridge 28 is formed by the adjacent inner sides 30 and 32 respectively of the wells 24 and 26 extending at approximately 90° to each other and meeting at a rounded apex 34.

A pair of inlet tubes, respectively comprising a cardiotomy inlet 36 and a blood inlet 38, are sealed to the reservoir in communication with the bottom area of the chamber well 24. Each of these tubes 36 and 38 will include, in addition to the inner discharge end, lateral holes or outlets 40 directly communicating with the interior of the chamber well at the lowest-most points thereof to prevent blood hold-up or stagnation.

A pair of air vents or venting tubes 42 and 44 are sealed to the reservoir in communication with the upper end of the chamber 12 through the upper seam 20 thereof. These tubes 42 and 44 are generally vertically aligned over the inlet tubes 36 and 38 and comprise a gross air removal tube 42 communicating with the chamber 12 slightly below the apex of the peaked upper edge 20 and a smaller tube 44 at the apex for air removal during operation of the equipment.

Figure 3:
FIG. 3 is a cross-sectional detail taken substantially on a plane passing along line 3—3 in FIG. 1.

Noting the cross-sectional detail of FIG. 3, in conjunction with FIG. 1, one of the sheets from which the bag is formed has a pair of shallow generally rectangular grooves or channels 46 defined therein and aligned in depending relation to the two vent tubes 42 and 44. The grooves 46 terminate, at the lower ends thereof, in substantial lateral alignment with the rounded apex 34 of the ridge 28. These grooves, normally heat formed in the thermoplastic material, tend to assist in upwardly directing air flow toward the vents, and more particularly prevent the chamber from closing down on itself and creating air pockets. The width of the grooves can be from 0.010" to 1". The depth of the grooves will be 50% to 90% of the thickness of the sheet within which they are defined.

In order to enhance the movement of any contained air toward the upper vents, three vertically aligned diverters or flow diverting buttons 48 are provided in the chamber 12 laterally spaced between the innermost groove 46 and the ridge apex 34, and vertically spaced between the ridge apex 34 and the upper seam 20. Each of the diverters is oblong and approximately 0.75"×1.25". The diverters may be at any angle from horizontal to ve However, for maximum effectiveness, the diverters will be inclined upwardly toward the vents 42 and 44 at 30° to the horizontal, generally following the inclination of the overlying portion of the upper seam 20. As noted from the cross-sectional detail of FIG. 4, each of the diverters 48 is defined by directly heat welding the overlying sheets to each other. The specific configuration and orientation of the three diverters 48 divert or change the flow between the inlet and outlet wells in a manner which significantly contributes to the easing of any air entrained in the flowing blood toward the air vents 42 and 44, and to the top of the reservoir for removal by the vents as opposed to exiting through the blood outlet tube 50 communicating with the bottom of the outlet well 26. The action of the diverters, while changing the flow pattern to enhance movement of the air to the top of the chamber 12, does not adversely affect movement of the blood through the chamber. As illustrated, the outlet tube 50 can also incorporate lateral holes 52 therein immediately below the open inner end to avoid any blood holdup or stagnation within the bottom of the chamber well 26.

Figure 2:
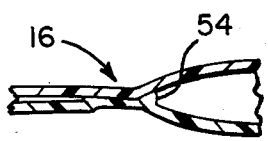
FIG. 2 is an enlarged cross-sectional detail taken substantially on a plane passing along line 2—2 in FIG. 1 and illustrating a typical chamber-defining seam.

A particularly troublesome area with regard to air entrapment is the seams of the storage chamber. In this regard, the normally provided seams, defined by high frequency welding, incorporate elongate constricted portions within which air bubbles tend to lodge and along which a smooth flow of blood is difficult. This problem is uniquely overcome by the specific formation of the chamber defining seams 16, 18, 20 and 22, in a manner so as to both enhance the smooth flow of blood therealong and eliminate any tendency for the trapping of air. More particularly, and noting the cross-sectional detail of FIG. 2 which is typical for all seams, the defined seam is specifically formed with a bead 54 which completely spans the interior angle between the sheets. The bead, thus formed, defines a fillet, forming a relatively wide generally planar surface without the normally restrictive infinitely narrowing joint normally associated with heat sealed soft shell bags which, by their very nature, tend to substantially restrict blood flow and trap air bubbles.

While, as noted in the Yoshida and Danby et al patents, the conventional high frequency welds tend to form joint beads, such beads normally bisect the joint angle and form even more restrictive grooves which, by their very nature, increase the likelihood of bubble entrapment. The bead 54, to the contrary, specifically defines a full width fillet between the sheets, leaving no restrictive channels. It is preferred that the formed beads 54 have a width within a range of from approximately the combined thickness of the two sheets to approximately double this combined thickness. When utilizing standard thickness sheets of 0.017", the formed beads are to be between 0.034" and 0.068" with the optimum range of between 0.043" and 0.064". As previously indicated, the formation of the seams with the specific parameter beads is preferably to be effected by RF welding.

Figure 4:
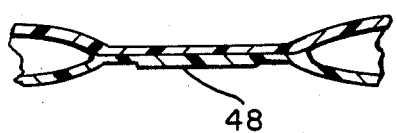
FIG. 4 is a cross-sectional detail taken substantially on a plane passing along line 4—4 in FIG. 1.

As will be recognized from the cross-sectional detail of Figure 4, the individual diverters are also to incorporate fillet-defining beads equivalent to and formed in the same manner as the beads 54 to encourage flow thereabout without bubble entrapment.

The reservoir 10 is completed by appropriate seaming about the rectangular periphery of the sheets, other than for the open lower ends of the two side sleeves 14 which selectively receive stiffeners 56 in the form of rigid PVC tubes. As will be noted, the sleeves 14 are outwardly spaced to each side of the storage chamber to avoid any direct stress transfer therebetween. Further, appropriate horizontal rigidifying weld lines 58 can be provided as desired.

The reservoir, as described, incorporates features both individually and in combination uniquely adapted to maximize air removal and maintaining an optimum blood movement system.

I claim:

1. A venous reservoir with an air removal enhancing means; said reservoir comprising two flexible sheets, a plurality of seams securing said sheets together peripherally thereabout and defining a closed blood storage chamber, said chamber, in a vertical orientation of said reservoir, having a top and a bottom, air venting means communicating with the top of said chamber, blood inlet means and blood outlet means communicating with said chamber below said air venting means, said blood outlet means being laterally spaced from said blood inlet means, each of said chamber-defining seams defining an angle between said sheets inwardly directed toward said chamber, said sheets, in the defined angle, diverging from a joinder point forming an angle apex, and a solid fillet means having a relatively wide generally planar surface without restrictive narrowing, said fillet means filling said angle between said sheets immediately inward of said joinder point and coextensive with the seam to define a flow-enhancing surface, eliminate the tendency for air bubbles to form, and reduce entrapment of bubbles along said seam.

2. The venous entrapment reservoir of claim 1 wherein said seams are defined by a welding of said sheets to each other.

3. The venous reservoir of claim 2 wherein said fillet means comprises a bead defined by the welding of the sheets.

4. The venous reservoir of claim 3 wherein said bead has a thickness equal to at least the combined thickness of the two sheets.

5. The venous reservoir of claim 4 wherein said bead has a maximum thickness of approximately twice the combined thicknesses of the two sheets.

6. The venous reservoir of claim 5 wherein said air venting means is in general vertical alignment with said blood inlet means, and a projecting portion in said chamber between said inlet means and said outlet means defined by said sheets and precluding direction lateral flow therebetween.

7. The venous reservoir of claim 6 including diverter means for diverting blood flow and directing entrained air to said air venting means, said diverter means being positioned in said chamber vertically between the top and bottom thereof and laterally between said inlet means and said outlet means.

8. The venous reservoir of claim 7 wherein said diverter means comprises multiple vertically spaced diverters, each defined by a welded seam securing the sheets together.

9. The venous reservoir of claim 8 wherein each of said diverters is elongate and upwardly inclined toward said air venting means.

10. The venous reservoir of claim 9 wherein the sheets at each diverter seam diverge from a joinder point and define an angle inwardly directed toward said chamber, and a solid fillet filling said angle immediately inward of said joinder point of each diverters seam to define a flow-enhancing surface therealong.

11. The venous reservoir of claim 10 including air guiding channel means defined vertically along the inner surface of one of said sheets generally vertically aligned between said blood inlet means and said air venting means.

12. The venous reservoir of claim 11 wherein said channel means communicate directly with said venting means.

13. The venous reservoir of claim 12 including a pair of vertical sleeves defined between said sheets to opposed sides of said chamber, and stiffener means received in said sleeves.

14. The venous reservoir of claim 13 wherein said welding is radio frequency welding.

15. The venous reservoir of claim 5 wherein said bead has a thickness within the range of 0.043" to 0.064".

16. The venous reservoir of claim 1 wherein said air venting means is in general vertical alignment with said blood inlet means, and a projecting portion in said chamber between said inlet means and said outlet means defined by said sheets and precluding direct lateral flow therebetween.

17. The venous reservoir of claim 16 including air guiding channel means defined vertically along and within the inner surface of one of said sheets generally vertically aligned between said blood inlet means and said air venting means.

18. The venous reservoir of claim 1 including diverter means for diverting blood flow and directing entrained air to said air venting means, said diverter means being positioned in said chamber vertically between the top and bottom thereof and laterally between said inlet means and said outlet means.

19. The venous reservoir of claim 18 wherein said diverter means comprises multiple vertically spaced diverters, each defined by a welded seam securing the sheets together inward spaced from the seams peripherally about the sheets.

20. A venous reservoir with air removal enhancing means; said reservoir comprising two flexible sheets, a plurality of seams securing said sheets together peripherally thereabout and defining a closed blood storage chamber, said chamber, in a vertical orientation of said reservoir, having a top and a bottom, air venting means communicating with the top of said chamber, blood inlet means and blood outlet means communicating with said chamber below said air venting means, said blood outlet means being laterally spaced from said blood inlet means, said air venting means being in general vertical alignment with said blood inlet means, and a diverter having a continuous peripheral seam for diverting blood flow and directing entrained air to said air venting means, said diverter being positioned entirely in said blood storage chamber, said diverter being spaced laterally inward of all peripheral seams in said blood storage chamber, said diverter being vertically between the air venting means and the blood inlet means and blood outlet means, and laterally inwardly spaced between said inlet means and said outlet means for flow in opposite directions about said diverter, and a central ridge between said blood inlet means and said blood outlet means to direct flow toward said diverter.

21. The venous reservoir of claim 20 including multiple separate vertically spaced diverters, each defined by a continuous peripheral welded seam securing the sheets together.

22. The venous reservoir of claim 21 wherein each said diverter is elongate and upwardly inclined toward said air venting means, and terminates laterally inward of said air venting means.

23. The venous reservoir of claim 22 wherein the sheets along each diverter seam diverge from a joinder point and define an angle inwardly directed toward said chamber, and a solid fillet filling said angle immediately inward of said joinder point to define a flow-enhancing surface along the diverter seam.

24. The venous reservoir of claim 23 including air guiding channel means defined vertically along the inner surface of one of said sheets generally vertically aligned between said blood inlet means and said air venting means.

25. The venous reservoir of claim 24 wherein said channel means communicate directly with said venting means.

26. The venous reservoir of claim 23 wherein each of said chamber-defining seams defines an angle between said sheets inwardly directed toward said chamber, said sheets, in defining said angle, diverging from a joinder point forming an angle apex, and a solid fillet spanning said angle between said sheets outward of said apex and coextensive with the chamber defining seam to define a flow-enhancing surface along said chamber defining seam.

* * * * *